United States Patent [19]
Yanagi et al.

[11] 4,448,996
[45] May 15, 1984

[54] PROCESS FOR PREPARING TERTIARY AMINES

[75] Inventors: Yoshio Yanagi; Kunikazu Yoneyama; Hiroyuki Omori, all of Yokkaichi, Japan

[73] Assignee: Mitsubishi Petrochemical Co., Ltd., Mie, Japan

[21] Appl. No.: 449,859

[22] Filed: Dec. 15, 1982

[30] Foreign Application Priority Data

Dec. 15, 1981 [JP] Japan .................................. 56-201986
Apr. 19, 1982 [JP] Japan .................................. 57-65067

[51] Int. Cl.³ ............................................. C07C 85/00
[52] U.S. Cl. .................................................... 564/467
[58] Field of Search ......................................... 564/467

[56] References Cited

U.S. PATENT DOCUMENTS 4,250,115  2/1981  Imai ................................. 564/467 X
4,292,242  9/1981  Laine .............................. 564/467 X
4,317,932  3/1982  Jachimowicz .................. 564/467 X Primary Examiner—Paul F. Shaver
Attorney, Agent, or Firm—Oblon, Fisher, Spivak, McClelland & Maier

[57] ABSTRACT

Tertiary amines are prepared by reacting a long-chain olefin with carbon monoxide, hydrogen, and a primary or secondary amine in the presence of a catalyst composed of a rhodium- and/or ruthenium-containing compound using a specific solvent, followed by phase separation of the reaction product. This process facilitates recovery and re-use of the expensive catalysts.

14 Claims, No Drawings

PROCESS FOR PREPARING TERTIARY AMINES

BACKGROUND OF THE INVENTION

1. Field of the Invention

The present invention relates to a process for preparing a tertiary amine having a long-chain alkyl group or groups and, more particularly, to a process for preparing a tertiary amine having one or two long-chain alkyl groups by the catalytic reaction of a long-chain olefin, carbon monoxide, hydrogen, and a primary or secondary amine.

2. Description of the Prior Art

Higher amines having a long-chain alkyl group or groups and derivatives thereof are useful, because of their structure, in a variety of applicatons such as intermediates for emulsifiers, rust inhibitors, and fabric-softeners and finishing agents, and the like. At present, most of them are commercially produced from natural fatty acids such as coconut oil, palm oil, beef tallow, and the like.

On the other hand, it is also known that tertiary amines can be synthesized from long-chain olefins, carbon monoxide, hydrogen, and primary or secondary amines. For example, Japanese Patent Publication No. 9527/66 discloses a one-stage process for preparing a tertiary amine from an olefin, carbon monoxide, hydrogen, and a secondary amine by using a catalyst comprising tri(hydrocarbyl)phosphine and cobalt carbonyl. However, this process is not necessarily effective for preparing the desired tertiary amines because it concurrently produces a large amount of alcohol as a by-product.

Helvetica Chimica Acta. vol. 54 (1971), pp. 1440–1445 and U.S. Pat. No. 3,947,458 each disclose a process for producing amines from an olefin, carbon monoxide, water and a nitrogen-containing compound using a catalyst composed of pentacarbonyliron and a rhodium compound. This process provides amines in considerably high yield, but it requires pure carbon monoxide as a reactant instead of a cheap gaseous mixture of hydrogen and carbon monoxide. It also requires the recovery of expensive rhodium compound.

Japanese Patent Application (OPI) No. 88812/74 discloses a process for producing tertiary amines by reacting an olefin, carbon monoxide, hydrogen and a secondary amine in the presence of a complex of a Group VIII metal complexed with a ligand containing an electron-donor atom such as oxygen, nitrogen or sulfur. This process also provides desired amines in extremely good yields, but problems with it in industrial practice center on the recovery and re-use of the expensive Group VIII metals rhodium and ruthenium which are used in considerably large amounts.

The reference provides no discussion of the problems with this reaction. That is, in processes for synthesizing higher amines having at least one long-chain alkyl group from long-chain olefins, the use of comparatively inexpensive cobalt or other Group VIII metals results in such a low reaction selectivity that the desired amines are produced only in low yields, whereas the use of expensive metal compounds such as rhodium compounds is so costly that it is not necessarily advantageous from an industrial point of view though it provides amines in high yields.

Accordingly, if the one-stage industrial process of synthesizing higher amines having at least one long-chain alkyl group from olefin in high yields using an expensive catalyst such as rhodium is to be practicaly realized, techniques of recovery and re-use of the expensive catalyst must be established.

Various processes have been proposed in the past for the recovery of rhodiun catalysts used in hydroformylation reactions and the like as follows:

(1) A process in which the reaction product is separated from a catalyst by evaporation or distillation (Japanese Patent Application (OPI) No. 125103/77);

(2) A process in which product aldehyde is separated from the reaction by extraction with a polar solvent such as water (Japanese Patent Application (OPI) No. 29412/76);

(3) A process in which rhodium complex is separated by adsorption (Japanese Patent Application (OPI) No. 62936/75); and (4) A process in which the reaction product is separated by using a membrane of, for example, silicone rubber or cellulose. Although process (1) above is applicable when the reaction product is a low-boiling lower aldehyde and when the catalyst is a rhodium complex modified with, for example, triphenylphosphine which has a comparatively high heat stability, attemped aplication of the process for the production of high-boiling higher amines, the end products of the present invention, results in many problems. Process (2) described above cannot be applied to higher amines having only a low water solubility. Adsorption process (3), when applied to an industrial process for the production of higher aldehydes, is not effective for producing nitrogen-containing compounds such as amines which can adversely affect the adsorbent. Further, process (4), which utilizes membrane separation, requires that the difference in molecular size between the reaction product and the catalyst complex be sufficient, and it is not effective for separating higher amine products having a comparatively large molecular size.

In order to advantageously practice the one-stage process of preparing tertiary amines having at least one long-chain alkyl group from olefins on an industrial scale, it is necessary that techniques be established for the recovery of expensive catalysts such as rhodium by which the end product is obtained in high yield, from a reaction product for re-use. However, it is not possible to avoid decomposition or loss of portions of the expensive complex during the treatment. The amount of the decomposed or lost catalyst, even a trace amount, has a serious affect on catalyst cost in the case of expensive Group VIII metals such as rhodium. Moreover, the amount of decomposed or lost complex catalyst usually increases as its concentration increases. Accordingly, the reaction is desirably conducted at as low a catalyst concentration as possible. However, when a rhodium-containing catalyst such as $RhCl_3.3H_2O$ is used as the catalyst, the presence of the catalyst in decreased concentration results in a decelerated reaction, which in turn results in a decreased conversion of olefin and, in addition deterioration of reaction selectivity. Thus, aldehydes, intermediates of the end products of tertiary amines, are produced in large quantities in the reaction zone. This results in a sharp increase in the amount of heavy substances formed upon condensation of the aldehydes or it results in the production of large amounts of impurities such as amines having unsaturated alkyl groups or imines having carbon-nitrogen double bonds other than the desired amines. Therefore, there is no advantage to be gained by decreasing the rhodium concentration in the reaction, and it is necessary to keep the rhodium concentration at a definite level in order to avoid decreases in reaction selectivity. A need therefore continues to exist for an improved technique of recovering and reusing expensive noble metal catalysts used in the synthesis of tertiary amines.

SUMMARY OF THE INVENTION

Accordingly, one object of the present invention is to provide a method of synthesizing tertiary amines by a catalytic method in which the expensive noble metal catalyst can be effectively recovered and reused.

Briefly, this and other objects of the present invention as hereinafter will become more readily apparent can be attained in a method of preparing a tertiary amine having at least one long-chain alkyl group by reacting a long-chain olefin having 8 to 30 carbon atoms, carbon monoxide, hydrogen, and a primary or secondary amine in the presence of a rhodium based catalyst and/or a ruthenium based catalyst in the presence of a solvent of an alcohol selected from the group consisting of monohydric alcohols containing 2 to 3 carbon atoms, dihydric alcohols containing 3 to 6 carbon atoms, trihydric alcohols containing 3 to 6 carbon atoms, intermolecular dehydration condensates of dihydric or trihydric alcohols containing 2 to 3 carbon atoms and mixtures of said alcohol and water, and allowing the reaction medium to separate into an amine phase containing the product tertiary amine and a solvent phase containing the catalyst.

DETAILED DESCRIPTION OF THE PREFERRED EMBODIMENTS

As a result of intensive investigations to find an industrially advantageous process for preparing higher amines, it has been found that when the present synthesis reaction is conducted with a specific alcohol as a solvent, the reaction solution separates, upon completion of the reaction, into a phase containing the product higher amine as the major component and a phase containing the used solvent as the major component, and that the used complex catalyst, for example, rhodium, substantially exists in the solvent phase and still possesses enough catalytic activity to be re-used in the reaction.

The catalyst which is used in the present invention is a compound of rhodium and/or ruthenium, and is used in the form of a halide, nitrate, halocarbonyl or carbonyl complex. Suitable examples thereof include rhodium chloride, rhodium nitrate, rhodium bromide, rhodium iodide, chlorodicarbonylrhodium dimer, rhodium carbonyl, ruthenium chloride, ruthenium nitrate, ruthenium bromide, ruthenium iodide, dichlorotricarbonylruthenium dimer, ruthenium carbonyl, and the like.

The rhodium or ruthenium catalysts are used in amounts of 1 mole per 100 to 20,000 moles of the olefin reactant. They can be used in greater relative amounts, i.e., in amounts of more than 1 mole per 100 moles of the olefin reactant, with no harm, however, with no economic advantage; whereas when the catalysts are used in amounts less than the indicated range, a deceleration of the reaction occurs accompanied by a sharp deterioration in reaction selectivity, making effective practice of the present invention difficult.

Most preferably, 1 mole of the catalyst is used per 500 to 10,000 moles of the olefin reactant.

When both rhodium and ruthenium compounds are used as the catalyst, the rhodium catalyst is used in an amount of 1 mole per 300 to 50,000 moles of the olefin reactant. Where the rhodium compound is used alone as the catalyst, the lower limit of the amount of the rhodium compound is 1 mole per 20,000 moles of the olefin reactant. If the relative rhodium concentration is less than the value indicated, conversion of olefin decreases because of deceleration of the rate of reaction with concurrent marked deterioration of reaction selectivity. These factors result in a sharp increase in aldehyde and heavy substance by-product formation. On the other hand, the amount of the olefin reactant can be increased up to about 50,000 moles per mole of the rhodium compound without a decrease in selectivity suffered because of a deceleration in the rate of reaction, by the combined use of a ruthenium compound with the rhodium compound. Of course, a deceleration in the rate of reaction is unavoidable as the concentration of the rhodium compound decreases, but the combined use of the ruthenium compound and the rhodium compound minimizes the reduction in selectivity to the desired amine and suppresses formation of aldehydes and heavy substances. The use of olefin reactant in an amount of more than 50,000 moles per mole of the rhodium compound is not practical because of the extremely slow reaction rate. On the other hand, the use of olefin reactant in an amount of less than 300 moles per mole of the rhodium compound is not necessarily harmful, but high concentration of the rhodium compound is liable to lead to an increase in loss of the catalyst without any corresponding advantage, thus being of no economic advantage.

The amount of the ruthenium compound employed in combination with the rhodium compound should be 0.1 to 100 moles per mole of the rhodium compound. If the amount of the ruthenium compound is less than 0.1 mole per mole of the rhodium compound, no particular effect can be obtained in comparison to the case in which the rhodium compound alone is used, and hence, when the concentration of the rhodium compound is low, the reaction selectivity sharply deteriorates. On the other hand, if the amount of ruthenium compound is more than 100 moles per mole of the rhodium compound, the ruthenium compound tends to decrease the activity of the rhodium catalyst for the hydroformylation of an olefin. Moreover, when the rhodium compound concentration is low, the conversion of olefin sharply decreases, and thus the use of such an amount of the ruthenium compound is economically disadvantageous especially in view of the increased amount of the ruthenium compound used.

When both the rhodium and ruthenium compounds are used as the catalyst, the preferred amount of the rhodium compound is 1 mole per 500 to 35,000 moles of the olefin reactant, more preferably 1 mole per 2,000 to 25,000 moles of the olefin reactant. In this case, the ruthenium compound is used in an amount of 0.1 to 50 moles, particularly 0.2 to 30 moles per mole of the rhodium compound.

The starting long-chain olefins used in the present invention are olefinically unsaturated compounds having a hydrocarbyl strucure, and preferred olefins are those which have a straight-chain hydrocarbyl structure containing 8 to 30 carbon atoms. Suitable straight-chain olefins include ethylene oligomers obtained from ethylene which have terminal double bonds, and long-chain olefins having internal double bonds and obtained by the catalytic dehydrogenation of straight-chain hydrocarbons obtained from kerosene and gas oil fractions or by isomerization or disproportionation of an α-olefin such as ethylene oligomer.

The primary or secondary amine used as the starting material is that one which yields the desired higher amines without any particular restriction. For example, when the end product is a long-chain alkyldimethylamine or -diethylamine which is an intermediate for fabric-softening and finishing agents, dimethylamine or diethylamine is chosen as the secondary amine. When the end product is a di-long-chain alkyl-methylamine or -ethylamine, methylamine or ethylamine is selected as the primary amine.

The mole ratio of the starting olefin to the starting amine in synthesizing the mono-long-chain alkyl type tertiary amine from a secondary amine is different from the ratio needed when synthesizing a di-long-chain alkyl type tertiary amine from a primary amine. In the former case, the mole ratio of olefin to secondary amine is at least 1:1, preferably 1:1 to 1:3 and, in the latter case, the mole ratio of olefin to primary amine must fall within the range of 1.5 to 2.5:1 with the range of about 2:1 being particularly preferred. When using primary amines, a large amount of primary amine is liable to result in the formation of a by-product of a mono-long-chain alkyl type secondary amine, and the use of a small amount of primary amine leads to the formation of intermediate aldehyde or heavy substances as by-products, thereby resulting in a decrease in the yield of the desired tertiary amine.

A specific alcohol is used as the solvent medium of the present reaction. Such alcohols easily undergo phase separation from amines upon completion of the reaction and serve to suppress dissolution of the rhodium or ruthenium compound catalyst into the amine phase.

Phase separation between the tertiary amine product and the alcohol used as the solvent is somewhat influenced by the length of the carbon chain of the long-chain alkyl group in the tertiary amine. That is, as the carbon chain length becomes shorter, compatibility of the amine with the alcohol increases, and hence, where the compatibility is high, it is preferable to use an alcohol having high polarity. When the polarity of the solvent selected is insufficient, it takes an extended period of time to complete phase separation of the reaction product which in turn leads to an increase in the amount of catalyst dissolved into a produced amine. In this case, replacement of the solvent by a solvent having a higher polarity or addition of a polar solvent such as water to the reaction system aids in improving the separation process. When the carbon chain length of the long-chain alkyl group in the amine product is long enough, or when the product amine is a di-long-chain type even when the length of each alkyl chain is not long enough, good phase separation can be generally attained.

Suitable alcohols which can be used as the solvent in the present invention include monohydric alcohols having 1 to 3 carbon atoms such as methanol, ethanol, n-propanol, and isopropanol; dihydric alcohols containing 2 to 6 carbon atoms such as ethylene glycol, propylene glycol, and the like, trihydric alcohols containing 3 to 6 carbon atoms such as glycerin, trimethylolpropane and the like; intermolecular dehydration condensates of dihydric alcohols containing 2 to 3 carbon atoms such as diethylene glycol, triethylene glycol, tetraethylene glycol, dipropylene glycol, tripropylene glycol, and the like; and polyethylene glycol, polypropylene glycol, or block or random polymers of ethylene glycol and propylene glycol, having a mean molecular weight of 2,000 or less.

Solvents which have some degree of polarity similar to the above-described alcohols and which cause good phase separation from the product amine include N,N-dimethylformamide, N,N-dimethylacetamide, sulfolane, dimethylsulfone, and the like.

The amount of the solvent used is not particularly limited. However, when the solvent is used in an amount of more than that is necessary, the yield of product decreases per unit volume of the reactor and the relative weight of the produced amine is reduced which leads to more difficult phase separation. In addition, the amount of the catalyst used must be increased in order to obtain a suitable catalyst concentration. On the other hand, if the amount of the solvent is extremely small, the phase separation becomes difficult because of the relatively small amounts of the same compared to the product amine, and dissolution of the catalyst into the product amine phase increases, which hinders re-use of the catalyst. Therefore, the solvent is usually used in an amount of 20 to 70 parts by weight per 100 parts by weight of the sum of the olefin and primary or secondary amine charged as the reactants. Preferably, from 30 to 50 parts by weight of the solvent are used per 100 parts by weight of the sum of the olefin and amine reactants.

The reaction conditions for the synthesis of tertiary amines by the present invention are a temperature of about 70° to about 240° C. and a pressure of about 30 to about 300 atmospheres, with preferred temperature and pressure ranges being 100° to 200° C. and 60 to 200 amospheres, respectively. The substantial portion of the vapor over the reaction is carbon monoxide and hydrogen. In some cases, an inert gas such as nitrogen, helium or methane may be added to the system at the same time. The mole ratio of hydrogen to carbon monoxide can be changed over a wide range but, in many cases, good conversion of olefin and good yield of tertiary amine can be attained by using 1.5 to 2.0 moles of hydrogen per mole of carbon monoxide.

The reaction is carried out with agitation, usually stirring. After completion of the reaction, the reaction solution upon standing separates into an upper phase rich in the product amine and a lower phase containing the solvent as the major component. The separated solvent phase contains most of the catalyst used in the reaction, and hence the reaction can be repeated by adding an olefin reactant and an amine reactant to the solvent phase. The catalyst present in the solvent phase possesses sufficient catalytic activity.

Unlike conventional separation techniques such as distillation, the process of the present invention eliminates the necessity of applying heat to the catalyst because recovery of the catalyst is conducted by phase separation and, as a result, the catalyst does not undergo denaturation nor deterioration by heat. In addition, the catalyst is recovered together with the phase-separated solvent, and therefore it can be re-used for the next reaction with no particular procedure. This advantage is extremely effective for the reaction of the present method of synthesizing tertiary amines having at least one long-chain alkyl group from olefin, carbon monoxide, hydrogen, and an amine because a highly active rhodium complex not containing a trivalent phosphorous compound such as triphenylphosphine is used, said hydridocarbonyltris-(triphenylphosphine) rhodium having a comparatively low heat stability, and because the higher amine reaction product has a comparatively high boiling point.

Another advantage of the present invention is that, since heavy substances produced as by-products of the reaction are essentially not present in the catalyst-containing, phase-separated solvent, they do not accumulate in the reaction system even when the catalyst-containing solvent is recycled. With the conventional process of separating the product by distillation, the heavy substances produced as by-products remain with the catalyst and are recycled to the reaction system together with the catalyst for re-use, thereby adversely affecting the reaction system. In order to control the accumulation of undesired by-products to a lower level limit, part of the recycled catalyst must be discharged from the reaction system with concurrent discharge of a portion of the effective catalyst. The process of the present invention does not require such a procedure and enables the utilization of the catalyst with great efficiency without encountering any trouble because of the recycling of heavy substances.

A further advantage of the present invention is that the stability of the catalyst in the reaction system is extremely high. That is, when the reaction of the present invention is conducted using benzene, toluene or the like as a solvent, part of the complex catalyst is decomposed to produced insolubles, whereas in the solvent system of the present invention, almost no insolubles are observed after the reaction. In addition, in comparison to a reaction system which uses a solvent which does not cause phase separation such as benzene or toluene, no insolubles are produced after conducting the reaction at a lower reaction pressure or, when the reaction pressure is the same, at higher temperatures. Accordingly, reaction conditions of a wider scope can be selected, which enables one to conduct the reaction under more advantageous conditions.

Advantages of the present invention obtained by using both a rhodium compound and a ruthenium compound as catalyst are described below.

A first advantage is that almost no aldehydes exist in a reaction zone regardless of the degree of conversion of an olefin reactant. Because of the absence of aldehydes, the substances which are separated and recovered from the reaction solution as unreacted materials for recycling to the reaction zone are substantially olefins, and separation of the long-chain alkyl group-containing amine product is easier than in the case where aldehydes are present. In addition, there are no problems encountered in the recycling procedure.

The present invention stands in contrast to other synthesis procedures where the substances to be recycled are unreacted olefin materials and by-product aldehydes which are difficult to separate from the product long-chain alkyl group-containing amine. In addition, the conventional recycling procedure results in a further increase in aldehyde concentration in the reaction zone with accompanying deterioration of reaction selectivity. Thus, the present invention enables the conversion of olefins to long-chain alkyl group-containing tertiary amines in high efficiency.

A second advantage of the present invention is that contamination of the long-chain alkyl group-containing tertiary amine fraction with impurities such as unsaturated amines or imines is suppressed down to an extremely low level. In fact, the end product obtained by the present process is so pure that an amine fraction obtained by mere distillation of the product is a suitable commercial product, and does not require further purification treatment such as, for example, hydrogenation, which is usually required.

The third advantage of the present invention is that the concentration of rhodium catalyst in the reaction can be decreased without loss in reaction selectivity and, as a result, the initial cost at the start of the reaction and decomposition and loss of rhodium upon recovery and re-use thereof can be reduced.

Having generally described this invention, a further understanding can be obtained by reference to certain specific examples which are provided herein for purposes of illustration only and are not intended to be limiting unless otherwise specified.

Additionally, percentages (%) in the following examples are based on the amount of charged olefin and are presented as mole percentages for theoretically producible amounts excluding the percentages of by-produced heavy substances (wt %) which are calculated according to the following equation:

Percentage of by-produced heavy substances (wt %) =

$$\frac{\text{Amount of produced heavy substances (g)}}{\text{Amount of charged olefin (g)}} \times 100.$$

EXAMPLE 1

An autoclave of 200 ml capacity was charged with 40 ml of methanol containing 0.014 g of $RhCl_3.3H_2O$, 30 g of 1-dodecene, and 20 g of diethylamine and was pressurized to 120 kg/cm$^2$ by a gas mixture of hydrogen and carbon monoxide in a molar ratio of 1.8:1.0, and the reaction was effected at 140° C. for about 3 hours.

After completion of the reaction, the contents separated into an upper phase rich in a product amine and a yellow lower phase containing the solvent as major component. Analysis of the composition of each phase revealed that the olefin conversion and the yield of a desired product of tridecyldiethylamine were 99% and 85%, respectively. The amine phase contained 7 ppm rhodium, and the solvent phase contained 160 ppm rhodium. Thus, most of the rhodium used was found to be present in the solvent phase.

A 30 g amount of 1-dodecene and 20 g of diethylamine were again added to 40 g of the above-described solvent phase, and the reaction was carried out in the same manner. As a result, an olefin conversion of 98% and an amine yield of 81% were obtained. Thus, the catalyst in the solvent phase upon re-use showed good activity and selectivity.

EXAMPLE 2

By using an aqueous ethanol solution having an ethanol-to-water weight ratio of 4/1 in place of methanol and otherwise following the procedures described in Example 1, the above reaction was conducted.

Upon completion of the reaction, the reaction solution separated into a product amine phase and a solvent phase as in Example 1. Analysis of the composition of each phase revealed that the olefin conversion and the yield of the desired tridecyldiethylamine product were 99% and 87%, respectively. The rhodium concentrations in the amine phase and in the solvent phase were 4 ppm and 130 ppm, respectively. Thus, most of the used rhodium was present in the solvent phase.

When 25 g of 1-dodecene and 18 g of diethylamine were added to 30 g of the solvent phase obtained and the reaction was effected in the same manner, an olefin conversion of 97% and an amine yield of 80% were obtained. Thus, activity and selectivity of the rhodium catalyst were maintained at the same levels.

EXAMPLE 3

A 40 ml ethanol solution containing 0.015 g of $RhCl_3.3H_2O$, 35 g of 1-hexadecene, and 18 g of diethylamine was charged in an autoclave of 200 ml capacity, and the reaction was conducted under the conditions described in Example 1. Upon completion of the reaction, the contents separated into a product amine phase and a yellow solvent phase. To this solvent phase again were added 1-hexadecene and diethylamine in the same amounts as used in the first run, followed by phase separation. Further, the starting materials were added to the resulting solvent phase to conduct the reaction. In such a manner, the reaction was repeated. The olefin conversions and the yields of heptadecyldiethylamine thus obtained are as follows.

|  | Olefin Conversion (%) | Yield of Amine (%) |
| --- | --- | --- |
| Fresh catalyst | 99 | 88 |
| Once used catalyst | 98 | 80 |
| Twice used catalyst | 94 | 70 |
| Thrice used catalyst | 90 | 68 |
| Four-times used catalyst | 84 | 51 |

EXAMPLE 4

As an olefin reactant, a $C_{12}$-internal olefin obtained by dehydrogenating n-dodecane and separating the product olefin through adsorption was used.

A 30 ml amount of an ethanol solution containing 0.012 g of $RhCl_3.3H_2O$, 30 g of the above-described $C_{12}$-n-olefin, and 15 g of dimethylamine was reacted under a pressure of 100 kg/cm$^2$ of a gas mixture of hydrogen and carbon monoxide having a hydrogen/carbon monoxide mole ratio of 1.7:1.0 at 150° C. for about 3 hours.

Upon completion of the reaction, the reaction solution separated into two phases as described in Examples 1 to 3. Analysis of the upper and lower phases revealed that the olefin conversion was 98%, and that the yield of product amine was 85%, which were about the same levels as the 1-olefin. The rhodium concentrations in the amine phase and in the solvent phase were 10 ppm and 120 ppm, respectively. Thus, most of the used rhodium was found to be present in the solvent phase.

EXAMPLE 5

An autoclave of 200 ml capacity was charged with 30 ml of methanol containing 0.010 g of $RhCl_3.3H_2O$, 35 g of 1-octene, and 7.7 g of monoethylamine and pressurized to 100 kg/cm$^2$ by a gas mixture of hydrogen and carbon monoxide having a hydrogen-to-carbon monoxide mole ratio of 1.8:1.0. The reaction was conducted at 140° C. for about 3 hours.

The reaction solution separated into an upper phase rich in product amine and a lower phase containing the solvent as a major component. Analysis of the composition of each phase revealed that the olefin conversion was 99%, and that the yield of dinonylethylamine amounted to 81%.

The concentrations of rhodium present in the upper and lower phases were 10 ppm and 110 ppm, respectively. Thus, most of the rhodium was found to be dissolved in the solvent phase.

EXAMPLE 6

A 40 ml ethylene glycol solution containing 0.017 g of $RhCl_3.3H_2O$, 30 g of 1-tetradecene, and 15 g of dimethylamine was charged into an autoclave of 200 ml capacity, and the reaction was conducted under the same conditions as described in Example 1.

Upon completion of the reaction, the contents separated into an almost transparent product amine phase and a green solvent phase. The solvent phase hardly contained any product pentadecyldimethylamine, and the concentration of rhodium in the product amine phase was as low as 3 ppm. Thus separation of the product amine from the catalyst was extremely good. Analysis of the composition of each phase revealed that the olefin conversion was 99%, and that the yield of desired pentadecyldimethylamine was 86%.

EXAMPLE 7

By using triethylene glycol as the solvent and otherwise following the procedures described in Example 6, the reaction was conducted.

Upon completion of the reaction, the contents separated into an almost colorless product amine phase and a pale green solvent phase. The rhodium concentration in the product amine phase was as low as 4 ppm, and the solvent phase was almost free of product pentadecyldimethylamine. Thus separation of the product from the catalyst was extremely good.

Analysis of the composition of each phase revealed that the olefin conversion and the yield of the desired pentadecyldimethylamine product were 99% and 83%, respectively.

EXAMPLE 8

By using 34 g of 1-hexadecene and 20 g of diethylamine as reactants and polyethylene glycol having a mean molecular weight of 600 as a solvent and otherwise following the procedures described in Example 6, a reaction was carried out.

Upon completion of the reaction, the contents separated into a colorless, transparent product amine phase and a pale yellow solvent phase. The product amine phase hardly contained any rhodium, and the solvent phase did not contain a detectable amount of the product amine. Thus separation of the catalyst from the product was almost complete.

Analysis of the composition of each phase revealed that the olefin conversion and the yield of the desired heptadecyldiethylamine product were 98% and 86%, respectively.

To 40 g of the solvent phase were added 1-hexadecene and diethylamine in amounts employed in the first run, and the reaction was repeated three times. The olefin conversions and the yields of the obtained amine were as shown below.

|  | Olefin Conversion (%) | Yield of Amine (%) |
| --- | --- | --- |
| Fresh catalyst | 98 | 86 |
| Once used catalyst | 98 | 83 |
| Twice used catalyst | 98 | 81 |
| Thrice used catalyst | 98 | 75 |

EXAMPLE 9

By using propylene glycol as a solvent and otherwise following the procedures described in Example 6, the reaction was conducted.

Phase separation of the reaction solution into a product amine phase and a solvent phase was good. The concentration of rhodium in the product amine phase was as low as 5 ppm, and therefore most of the catalyst was present in the solvent phase. Analysis of the composition of each phase revealed that the olefin conversion and the yield of the desired pentadecyldimethylamine product were 99% and 86%, respectively.

EXAMPLE 10

By using 1,4-butanediol as the solvent and 36 g of 1-octadecene and 20 g of dimethylamine as reactants and otherwise following the procedures described in Example 6, the reaction was carried out.

On completion of the reaction, the contents separated into a product amine phase containing a nonadecyldimethylamine product as the major component and a solvent phase mainly comprising 1,4-butanediol.

Analysis of the composition of each phase revealed that the olefin conversion and the yield of nonadecyldimethylamine were 98% and 82%, respectively.

EXAMPLE 11

An autoclave of 200 ml capacity was charged with 40 ml of glycerin containing 0.020 g of $RhCl_3.3H_2O$, 25 g of 1-decene, and 30 g of diethylamine and was pressurized to 130 kg/cm$^2$ by a gas mixture composed of hydrogen and carbon monoxide having a mole ratio of 1.7:1.0, and the reaction was conducted at 140° C. for about 2 hours.

Upon completion of the reaction, the contents separated into an almost colorless product amine phase and a solvent phase containing glycerin as the major component. The solvent phase hardly contained any undecyldiethylamine product, and rhodium was hardly detected in the product amine phase. Thus separation of the product amine from the rhodium catalyst was almost complete.

Analysis of the composition of each phase revealed that the olefin conversion and the yield of the desired undecyldiethylamine product were 99% and 89%, respectively.

EXAMPLE 12

By using diglycerol, a dehydrated condensate of glycerin, as the solvent and otherwise following the procedures described in Example 11, the reaction was conducted.

Upon completion of the reaction, phase separation took place in a short time, and the resulting solvent phase contained almost no product amine.

Analysis of the composition revealed that the olefin conversion and the yield of the desired undecyldiethylamine product were 98% and 86%, respectively.

When 20 g of 1-decene and 25 g of diethylamine were added to 35 g of the solvent phase and the reaction was conducted again, the desired amine was obtained in a yield of 79% with an olefin conversion of 96%.

EXAMPLE 13

An autoclave of 200 ml capacity was charged with 40 ml of methanol containing 0.050 g of $RuCl_3.3H_2O$, 35 g of 1-hexadecene, and 20 g of dimethylamine and was pressurized to 150 kg/cm$^2$ by a gas mixture composed of hydrogen and carbon monoxide in mole ratio of 1.8:1.0, and the reaction was conducted at 160° C. for about 5 hours.

Upon completion of the reaction the contents separated into a phase rich in a product amine and unreacted olefin and a solvent phase mainly composed of methanol. Analysis of the composition of each phase revealed that the olefin conversion and the yield of the amine were 38% and 33%, respectively.

EXAMPLE 14

A 40 ml amount of ethylene glycol containing 0.120 g of $RuCl_3.3H_2O$, 30 g of 1-tetradecene, and 25 g of diethylamine was charged into an autoclave of 200 ml capacity, and the reaction was conducted under the same conditions as described in Example 13.

Upon completion of the reaction, the contents separated into a phase rich in a product amine and unreacted olefin and a solvent phase mainly comprising ethylene glycol. The solvent phase contained the unreacted olefin and the product amine in extremely slight amounts.

To 30 g of this solvent phase was added 20 g of 1-tetradecene and 15 g of diethylamine, and the reaction was repeated under the same conditions. The contents, on being removed, separated into two phases as in the first run.

Analysis of the composition of the product amine phase revealed that the olefin conversion and the yield of product amine in the above-described two reactions are as follows. Thus, it is seen that the process of the present invention can be applied to the case of using the ruthenium-containing compound as a catalyst similar to the case in which the rhodium-containing compound is used as the catalyst.

|  | Olefin Conversion (%) | Yield of Amine (%) |
| --- | --- | --- |
| Fresh catalyst | 48 | 42 |
| Once used catalyst | 43 | 36 |

COMPARATIVE EXAMPLE 1

An autoclave of 200 ml capacity was charged with 40 ml of n-butanol containing 0.015 g of $RhCl_3.3H_2O$, 34 g of 1-octadecene, and 25 g of diethylamine and was pressurized to 110 kg/cm$^2$ by a gas mixture composed of hydrogen and carbon monoxide in a molar ratio of 1.6:1.0, and the reaction was conducted at 150° C. for about 2 hours.

The olefin conversion and the yield of the desired nonadecyldiethylamine product were as high as 98% and 83%, respectively. However, phase separation of the contents did not take place.

EXAMPLE 15

An autoclave of 200 ml capacity was charged with 32 g of ethylene glycol containing 0.0028 g of $RhCl_3.3H_2O$ and 0.032 g of $RuCl_3.3H_2O$, 34 g of 1-dodecene, and 20 g of diethylamine, and was pressurized up to 120 kg/cm$^2$ G by a gas mixture composed of hydrogen and carbon monoxide in a mole ratio of 1.8:1.0, then the reaction was conducted at 150° C. for about 2 hours.

Upon completion of the reaction, the contents separated into an upper phase containing product amine and unreacted olefin as the major components and a lower phase comprising the catalysts and the solvent. Analysis of the composition of each phase revealed that the olefin conversion and the yield of the desired tridecyldiethylamine product were 52% and 49%, respectively, and that undesirable aldehydes and heavy substances were barely detected.

EXAMPLE 16

By using 32 g of ethylene glycol containing 0.0025 g of $RhCl_3.3H_2O$ and 0.0110 g of $RuCl_3.3H_2O$ and otherwise following the procedures described in Example 15, the reaction was carried out.

As a result, the olefin conversion, the yield of the desired tridecyldiethylamine product, and the yield of undesired aldehyde were 61%, 56%, and 0.7%, respectively, and heavy by-products were essentially not present.

EXAMPLE 17

By using 32 g of ethylene glycol containing 0.0026 g of $RhCl_3.3H_2O$ and 0.0030 g of $RuCl_3.3H_2O$ and otherwise following the procedures described in Example 15, the reaction was conducted.

As a result, an olefin conversion of 64% and a desired tridecyldiethylamine yield of 60% were obtained, and heavy by-products were found to be produced in a yield of 0.5%.

EXAMPLE 18

The reaction was conducted in the same manner as described in Example 15 except that $RuCl_3.3H_2O$ was not used. Analysis of the reaction solution revealed that the yield of the $C_{13}$ hydrocarbyldiethylamine product and the yield of aldehyde were 31% and 12%, respectively, though the olefin conversion was 75%, and that the yield of heavy by-products amounted to 32%. Large amount of unsaturated amines were contained in the $C_{13}$ hydrocarbyldiethylamine product.

EXAMPLE 19

By using 32 g of ethylene glycol containing 0.024 g of $Rh(NO_3)_3.2H_2O$ and 0.030 g of $RuCl_3.3H_2O$ and otherwise following the procedures described in Example 15, the reaction was conducted.

Analysis conducted after the reaction revealed that the olefin conversion, the yield of desired tridecyldiethylamine, and the yield of undesired aldehyde were 93%, 73%, and 13%, respectively, and that heavy by-products were produced in a yield less than 3%.

EXAMPLE 20

By using 32 g of ethylene glycol containing 0.019 g of $RhCl_3.3H_2O$ and 0.050 g of $RuCl_3.3H_2O$ and otherwise following the procedures described in Example 1, a reaction was carried out.

Analysis conducted after the reaction revealed that the olefin conversion and the yield of desired tridecyldiethylamine were 85% and 82%, respectively, and that undesired aldehydes and heavy substances were hardly present in the reaction solution.

EXAMPLE 21

By using 32 g of polyethylene glycol having a mean molecular weight of 600 and containing 0.0076 g of $RhCl_3.3H_2O$ and 0.012 g of $RuCl_3.3H_2O$ and otherwise following the procedures described in Example 15, the reaction was carried out.

Analysis of the reaction solution revealed that the olefin conversion and the yield of desired tridecyldiethylamine were 75% and 71%, respectively, and that undesired aldehydes and heavy substances were hardly present in the reaction solution.

EXAMPLE 22

By using 32 g of polyethylene glycol having a mean molecular weight of 600 and containing 0.0081 g of $RhCl_3.3H_2O$ and 0.052 g of $RuCl_3.3H_2O$ and otherwise following the procedures described in Example 15, the reaction was carried out.

Analysis of the reaction solution indicated that the olefin conversion and the yield of desired tridecyldiethylamine were 62% and 59%, respectively, and that undesired aldehydes and heavy substances were hardly present in the reaction solution.

EXAMPLE 23

By using 32 g of ethylene glycol containing 0.0079 g of $RhCl_3.3H_2O$ and 0.0030 g of $RuCl_3.3H_2O$ and otherwise following the procedures described in Example 15, the reaction was carried out.

Analysis of the reaction solution indicated that the olefin conversion and the yield of desired tridecyldiethylamine were 83% and 75%, respectively, and that heavy by-products were produced in a yield of less than 1%.

The results obtained from Examples 15-23 are tabulated in Table 1.

EXAMPLE 24

An autoclave of 200 ml capacity was charged with 34 g of ethanol containing 0.0060 g of $RhCl_3.3H_2O$ and 0.040 g of $RuCl_3.3H_2O$, 30 g of 1-dodecene, and 20 g of diethylamine and was pressurized up to 140 kg/cm$^2$ G by a gas mixture composed of hydrogen and carbon monoxide in a mole ratio of 1.7:1.0, and the reaction was conducted at 140° C. for about 2 hours.

Analysis of the contents upon completion of the reaction revealed that the olefin conversion and the yield of desired tridecyldiethylamine were 83% and 83%, respectively, and that undesirable aldehydes and heavy substances were hardly present.

EXAMPLE 25

An autoclave of 200 ml capacity was charged with 35 g of ethylene glycol containing 0.0050 g of $RhCl_3.3H_2O$ and 0.060 g of $RuCl_3.3H_2O$, 34 g of 1-hexadecene, and 20 g of diethylamine and was pressurized up to 120 kg/cm$^2$ G by a gas mixture composed of hydrogen and carbon monoxide in a mole ratio of 1.8:1.0, and the reaction was conducted at 160° C. for about 3 hours.

Analysis of the contents revealed that the olefin conversion and the yield of desired heptadecyldiethylamine were 85% and 78%, respectively, and that undesired by-products such as aldehydes and heavy substances were hardly present in the reaction solution.

EXAMPLE 26

The reaction was conducted by using the catalystcontaining solvent phase obtained in Example 25. That is, 30 g of 1-hexadecene and 20 g of diethylamine were added to 32 g of the solvent phase, and the reaction was repeated in an autoclave of 200 ml capacity under the same conditions as in Example 25.

Analysis of the contents of the reactor after completion of the reaction indicated that the olefin conversion and the yield of desired heptadecyldiethylamine were 81% and 75%, respectively, and that undesired by-products such as aldehydes and heavy substances were hardly present in the reaction solution as described in Example 25.

EXAMPLE 27

An autoclave of 200 ml capacity was charged with 37 g of polyethylene glycol having a mean molecular weight of 600 and 0.0045 g of $RhCl_3.3H_2O$ and 0.080 g of $RuCl_3.3H_2O$, 35 g of 1-octadecene, and 19 g of diethylamine and was pressurized up to 150 kg/cm² G by a gas mixture composed of hydrogen and carbon monoxide in a mole ratio of 1.9:1.0, and the reaction was conducted at 160° C. for about 5 hours.

Upon completion of the reaction, the contents separated into an upper phase containing an almost colorless, transparent product amine and unreacted olefin and a yellow, lower solvent phase containing the catalysts.

Analysis of the composition of each phase revealed that the olefin conversion and the yield of desired nonadecyldiethylamine were 88% and 79%, respectively, and that aldehydes were hardly present.

EXAMPLE 28

A 30 g amount of 1-octadecene and 20 g of diethylamine were added to 34 g of the catalyst-containing solvent phase obtained in Example 27, and the reaction was again conducted under the same conditions as described in Example 27.

As a result, the desired nonadecyldiethylamine product was obtained in a yield of 76%, the olefin conversion being 83%. As in Example 27, extremely slight amounts of aldehydes were detected.

EXAMPLE 29

By using 32 g of ethylene glycol containing 0.028 g of $RuCl_3.3H_2O$ alone and otherwise following the procedures described in Example 15, the reaction was carried out.

Upon completion of the reaction, the contents were found to be a two-phase mixture comprising an upper phase mainly containing unreacted olefin and a product amine and lower phase containing most of the ruthenium catalyst.

Analysis of the composition of each phase revealed that the olefin conversion and the yield of desired tridecyldiethylamine were 14% and 12%, respectively.

The results obtained in Examples 24 to 29 are tabulated in Table 2.

TABLE 1

| | $RhCl_3$ (mmole) | $RuCl_3$ (mmole) | Olefin (mmole) | Olefin/Rh | Ru/Rh | Olefin Conversion (mole %) | Yield of Amine (mole %) | Yield of Aldehyde (mole %) | Heavy By-products (wt %) |
|---|---|---|---|---|---|---|---|---|---|
| Example 15 | $1.06 \times 10^{-2}$ | $12.21 \times 10^{-2}$ | 202 | 19100 | 11.5 | 52 | 49 | trace | trace |
| Example 16 | 0.95 | 4.20 | 202 | 21300 | 4.4 | 61 | 56 | 0.7 | trace |
| Example 17 | 0.98 | 1.15 | 202 | 20600 | 1.2 | 64 | 60 | 2 | 0.5 |
| Example 18 | 1.06 | 0 | 202 | 19100 | 0 | 75 | 31 | 12 | 32 |
| Example 19 | 7.20* | 11.45 | 202 | 2800 | 1.6 | 93 | 73 | 13 | 3 |
| Example 20 | 7.20 | 19.08 | 202 | 2800 | 2.7 | 85 | 82 | trace | trace |
| Example 21 | 2.88 | 4.58 | 202 | 7000 | 1.6 | 75 | 71 | trace | trace |
| Example 22 | 3.07 | 19.85 | 202 | 6600 | 6.5 | 62 | 59 | trace | trace |
| Example 23 | 2.99 | 1.15 | 202 | 6800 | 0.4 | 83 | 76 | 5 | 1 |

*nitrate salt
solvent: ethylene glycol
olefin reactant: 1-dodecene
reaction conditions: 150° C. in temperature; 120 kg/cm² in pressure; and 2 hours in reaction time

TABLE 2

| | Olefin | Solvent* | $RhCl_3$ (mmole) | $RuCl_3$ (mmole) | Olefin (mmole) | Olefin/Rh | Rh/Ru | Olefin Conversion (mole %) | Yield of Amine (mole %) | Yield of Aldehyde (mole %) | Heavy by-products (wt %) | Notes (reaction conditions) |
|---|---|---|---|---|---|---|---|---|---|---|---|---|
| Ex. 24 | α-$C_{12}$ | EtOH | $2.27 \times 10^{-2}$ | $15.27 \times 10^{-2}$ | 179 | 7900 | 6.7 | 83 | 78 | trace | trace | 140 kg/cm², 140° C., 2 hrs. |
| Ex. 25 | α-$C_{16}$ | EG | 1.89 | 22.90 | 152 | 8000 | 12.1 | 85 | 78 | trace | trace | 120 kg/cm², 160° C., 3 hrs. |
| Ex. 26 (using catalyst recovered in Ex. 25) | α-$C_{16}$ | EG | 1.89 | 22.90 | 134 | 7100 | 12.1 | 81 | 75 | trace | trace | 120 kg/cm², 160° C., 3 hrs. |
| Ex. 27 | α-$C_{18}$ | PEG | 1.70 | 30.53 | 139 | 8200 | 18.0 | 88 | 79 | trace | trace | 150 kg/cm², 160° C., 5 hrs. |
| Ex. 27 (using catalyst recovered in Ex. 27) | α-$C_{18}$ | PEG | 1.70 | 30.53 | 119 | 7000 | 18.0 | 83 | 76 | trace | trace | 150 kg/cm², 160° C., 5 hrs. |
| Ex. 29 | α-$C_{12}$ | EG | 0 | 10.69 | 202 | | | 14 | 12 | trace | trace | 120 kg/cm², |

TABLE 2-continued

|  | Olefin | Solvent* | RhCl₃ (mmole) | RuCl₃ (mmole) | Olefin (mmole) | Olefin/Rh | Rh/Ru | Olefin Conversion (mole %) | Yield of Amine (mole %) | Yield of Aldehyde (mole %) | Heavy by-products (wt %) | Notes (reaction conditions) |
|---|---|---|---|---|---|---|---|---|---|---|---|---|
|  |  |  |  |  |  |  |  |  |  |  |  | 150° C., 2 hrs. |

*EtOH: ethanol
EG: ethylene glycol
PEG: polymethylene glycol (mean molecular weight: 600)

Having now fully described the invention, it will be apparent to one of ordinary skill in the art that many changes and modifications can be made thereto without departing from the spirit or scope of the invention as set forth herein.

What is claimed as new and is intended to be secured by Letters Patent is:

1. In a process for the preparation of a tertiary amine having at least one long-chain alkyl group by the catalytic reaction of a long-chain olefin containing 8 to 30 carbon atoms, carbon monoxide, hydrogen, and a primary or secondary amine in the presence of a rhodium-based catalyst and/or a ruthenium-based catalyst, the improvement which comprises:

conducting said reaction in a solvent of an alcohol selected from the group consisting of monohydric alcohols containing 1 to 3 carbon atoms, dihydric alcohols containing 2 to 6 carbon atoms, trihydric alcohols containing 3 to 6 carbon atoms, intermolecular dehydrated condensates of dihydric or trihydric alcohols containing 2 to 3 carbon atoms and mixtures of said alcohol and water; and allowing the reaction solution to separate into an amine phase containing the product tertiary amine and a solvent phase containing the catalyst.

2. The process of claim 1, wherein said solvent phase containing the catalyst is recycled to the reaction zone.

3. The process of claim 1, wherein said intermolecular dehydrated condensate of a dihydric or trihydric alcohol containing 2 to 3 carbon atoms is polyethylene glycol, polypropylene glycol, or a block or random copolymer of ethylene glycol and propylene glycol, having a mean molecular weight of 2,000 or less, or diglycerol.

4. The process of claim 1, wherein said catalyst comprises a rhodium compound and a ruthenium compound.

5. The process of claim 4, wherein the amount of said olefin reactant is 300 to 50,000 moles per mole of the rhodium compound in said catalyst.

6. The process of claim 4, wherein the amount of said ruthenium compound is in the range of from 0.1 to 100 moles per mole of the rhodium compound in said catalyst.

7. The process of claim 1, wherein said rhodium or ruthenium catalyst is a halide or nitrate salt of the metal or is a halocarbonyl or carbonyl complex of the metal.

8. The process of claim 1, wherein the mole ratio of said olefin to said secondary amine is 1:1 to 1:3.

9. The process of claim 1, wherein the mole ratio of said olefin to said primary amine is 1.5 to 2.5:1.

10. The process of claim 1, wherein said solvent is employed in an amount of 20 to 70 parts by weight per 100 parts by weight of the sum of said olefin and said primary or secondary amine.

11. The process of claim 1, wherein said reaction is conducted at a temperature of 70°–240° C. under a pressure of 30 to 300 atmospheres.

12. The process of claim 1, wherein the gas over said reaction medium is primarily a mixture of carbon monoxide to hydrogen in a mole ratio of 1.5 to 2.0 moles of carbon monoxide per mole of hydrogen.

13. The process of claim 2, wherein said intermolecular dehydrated condensate of a dihydric or trihydric alcohol containing 2 to 3 carbon atoms is polyethylene glycol, polypropylene glycol, or a block or random copolymer of ethylene glycol and propylene glycol, having a mean molecular weight of 2,000 or less, or diglycerol.

14. The process of claim 5, wherein the amount of said ruthenium compound is in the range of from 0.1 to 100 moles per mole of the rhodium compound in said catalyst.

* * * * *